(12) United States Patent
Lesecq

(10) Patent No.: US 8,577,635 B2
(45) Date of Patent: Nov. 5, 2013

(54) CALIBRATING METHOD AND SYSTEM, RECORDING MEDIUM FOR THIS METHOD

(75) Inventor: Suzanne Lesecq, Froges (FR)

(73) Assignee: Commissariat a l'energie atomique et aux Energies Alternatives, Paris (FR)

( * ) Notice: Subject to any disclaimer, the term of this patent is extended or adjusted under 35 U.S.C. 154(b) by 258 days.

(21) Appl. No.: 13/074,066

(22) Filed: Mar. 29, 2011

(65) Prior Publication Data

US 2011/0238350 A1 Sep. 29, 2011

(30) Foreign Application Priority Data

Mar. 29, 2010 (FR) ...................................... 10 52261

(51) Int. Cl.
*G06F 19/00* (2011.01)
(52) U.S. Cl.
USPC .................................. 702/85; 703/2; 708/300
(58) Field of Classification Search
CPC .......... G06F 17/50; G06F 19/00; G05B 13/04
USPC ........................................................... 702/85
See application file for complete search history.

(56) References Cited

U.S. PATENT DOCUMENTS

| | | | |
|---|---|---|---|
| 6,285,971 B1 * | 9/2001 | Shah et al. ........................ 703/2 |
| 7,379,844 B2 * | 5/2008 | Lee et al. ...................... 702/181 |
| 7,460,916 B2 * | 12/2008 | Batruni ............................. 700/34 |
| 7,689,297 B2 * | 3/2010 | Batruni ............................. 700/40 |
| 8,027,741 B2 * | 9/2011 | Kahn ................................ 700/28 |
| 8,078,289 B2 * | 12/2011 | Stephenson et al. ............... 700/2 |
| 8,209,159 B2 * | 6/2012 | Bensch et al. ...................... 703/8 |
| 2003/0115232 A1 | 6/2003 | Lipp |
| 2003/0195404 A1 * | 10/2003 | Knobbe et al. ................. 600/365 |
| 2008/0000292 A1 * | 1/2008 | Abramovitch ................... 73/105 |
| 2010/0036613 A1 * | 2/2010 | Zeng et al. ...................... 701/220 |
| 2011/0125293 A1 * | 5/2011 | Havlena .......................... 700/30 |

FOREIGN PATENT DOCUMENTS

CA 2266282 9/2000

OTHER PUBLICATIONS

L. Ljung, "System Identification", p. 1033-1054, 1996 by CRC Press, Inc.*
W.Wu, et al., "Inferring hand motion from multi-cell recordings in motor conrtex using a Kalman filter", SAB 2002.*
Li et al. "Object Tracking Using an Adaptive Kalman Filter Combined with Mean Shift" *Optical Engineering*, 49(2): pp. 020503-1 to 020503-3 (Feb. 2010).
Gao et al. "Self-Tuning Multisensor Weighted Measurement Fusion Kalman Filter" *IEEE Transactions on Aerospace and Electronic Systems*, 45(1): 179-191 (Jan. 2009).
Akesson et al. "A Tool for Kalman Filter Tuning" *Computer Aided Chemical Engineering*, 24: 859-864 (2007).

* cited by examiner

*Primary Examiner* — Jonathan C Teixeira Moffat
*Assistant Examiner* — Ruihua Zhang
(74) *Attorney, Agent, or Firm* — Occhiuti & Rohlicek LLP

(57) ABSTRACT

A method for calibrating coefficients of an observer of a variable state of a physical system from measurements of physical quantities of the system, at different instants includes measuring a variable of the physical system at several instants, the variable being a function of a system state variable, and determining a vector of coefficients that minimizes a sum of the number of measurements of a square of a norm of a vector that is the difference between the measured variable and a function of the system state variable and the vector of coefficients. The minimization is subject to a constraint that the trajectory of the measured variable be within a corridor of uncertainty on either side of a trajectory of its estimate, at least for the measurement instants.

9 Claims, 1 Drawing Sheet

CALIBRATING METHOD AND SYSTEM, RECORDING MEDIUM FOR THIS METHOD

CROSS REFERENCE TO RELATED APPLICATIONS

Figure 1:
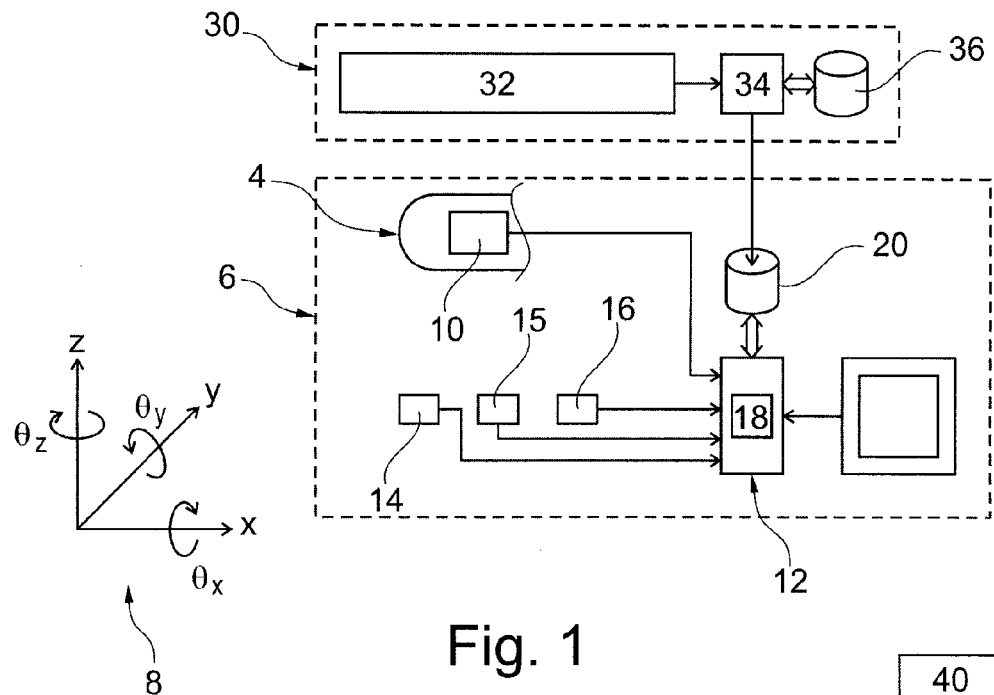

This application claims the benefit of the Mar. 29, 2010 priority date of French application FR1052261. The contents of the foregoing application are incorporated herein by reference.

The invention pertains to a method and system for calibrating coefficients of an observer of a variable state $x_k$ of a physical system. The invention also pertains to a recording medium to implement this method.

An observer estimates the state variable $x_k$ from measurements $y_k$ of physical quantities or magnitudes of this system where the index k identifies the instant of measurement.

There are known ways of calibrating the coefficients of an observer by successive experiments with different sets of coefficients until one set of coefficients gives the desired operation by this observer. Typically, the behavior desired for the observer is:

fast convergence towards the most exact possible estimation $\hat{x}_k$ of the variable $x_k$, and high stability.

This calibration by experiment is part of a heuristic approach. The calibration is often lengthy, and it is difficult to be certain that the best possible calibration of the observer has been obtained.

To resolve this problem, other alternative methods have been proposed. For example, the patent application CA 2 226 282 describes a method for calibrating coefficients of a Kalman filter by means of a neural network. However, these alternative methods are often as complex to implement as the method that uses experimentation.

The invention is therefore aimed at proposing a method of calibration that is simpler to implement.

Thus, an object of the invention is a method for calibrating coefficients of an observer comprising:

the measurement of a variable $z_k$ of the physical system at N different instants, this variable $z_k$ being a function of the state variable $x_k$;

the determining of a vector p of coefficients which minimizes the following criterion in complying with a predetermined set $\Delta$ of constraints:

$$\left\{ f(p) = \sum_{k=1}^{N} \|z_k - \phi(\hat{x}_k, p)\|^2 \right\}$$

where:

$\hat{x}_k$ is the estimation of the variable $x_k$ built by the observer calibrated with the coefficients of the vector p at the instant k;

$\phi$ is a known function which links the estimation $\hat{x}_k$ to an estimation $\hat{z}_k$ of the variable $z_k$;

$\|\ldots\|^2$ is a norm of the difference between $z_k$ and $\phi(\hat{x}_k, p)$, and the constraint or the constraints of the set $\Delta$ dictate that the trajectory of the variable $z_k$ should be included in a corridor of uncertainty situated on either side of the trajectory of the estimation $\hat{z}_k$ at least for the majority of the instants k.

The above method is used to determine the coefficients enabling an efficient functioning of the observer in a simple way and without recourse to different experiments. Furthermore, the coefficients thus determined make it possible to ensure that the criterion f(p) has been minimized.

Finally, the use of the set $\Delta$ takes account of the fact that there is an uncertainty on the estimation $\hat{z}_k$. Taking account of this uncertainty when determining the vector p that minimizes the criterion f(p) gives better calibration than if this uncertainty were not taken into account. In particular, aberrant approaches which could minimize the criterion f(p) are eliminated.

The embodiments of this calibration method may include one or more of the following characteristics:

the set $\Delta$ includes a constraint which dictates that the variable $z_k$ should be included between $\hat{z}_k-a$ and $\hat{z}_k+b$, where a and b are predetermined positive constants;

the constants a and b are proportional to a mean square deviation $\sigma_{\hat{z}_k}$ representing the uncertainty in the estimation $\hat{z}_k$;

the set $\Delta$ of constraints includes a constraint which dictates that the mean of the deviations between the variable $z_k$ and its estimation $\hat{z}_k$ should be below a predetermined threshold $S_1$;

the threshold $S_1$ is a function of the uncertainty on the estimation $\hat{z}_k$;

the observer is a Kalman filter, an extended Kalman filter or an Unscented Kalman Filter and the coefficients to be calibrated are coefficients of the covariance matrices R and Q of this filter;

the R and Q matrices are chosen to be diagonal matrices.

These embodiments of the calibration method furthermore have the following advantages:

dictating that the variable $z_k$ should be included between $\hat{z}_k-a$ and $\hat{z}_k+b$ reduces the space of search in which the vector p must be sought, thus accelerating the execution of this method;

using constants a and b proportional to the mean square deviation $\sigma_{\hat{z}_k}$ improves the calibration, using a constraint which dictates that the mean of the deviations in terms of absolute value between the variable $z_k$ and its estimation $\hat{z}_k$ should be below the threshold $S_1$ relaxes the dictated constraints thus facilitating the determination of a vector p;

using a threshold $S_1$ which is a function of the uncertainty of the estimation of $\hat{z}_k$ improves the calibration;

choosing diagonal R and Q matrices decreases the number of coefficients to be determined, thus facilitating the calibration.

An object of the invention is also an information-recording medium comprising instructions to implement the above method when the instructions are executed by a programmable electronic computer.

An object of the invention is also a system for calibrating coefficients of an observer of a state variable $x_k$ of a physical system from measurements $y_k$ of physical quantities of this system where the index k identifies the instant of measurement, the system comprising:

at least one sensor capable of measuring a variable $z_k$ of the physical system at N different instants, this variable $z_k$ being a function of the state variable $x_k$, and a computer capable of determining a vector p of coefficients which minimizes the following criterion in complying with a predetermined set $\Delta$ of constraints:

$$\left\{ f(p) = \sum_{k=1}^{N} \|z_k - \phi(\hat{x}_k, p)\|^2 \right\}$$

where:

$\hat{x}_k$ is the estimation of the variable $x_k$ built by the observer calibrated with the coefficients of the vector p at the instant k, $\phi$ is a known function which links the estimation $\hat{x}_k$ to an estimation $\hat{z}_k$ of the variable $z_k$, $\|\ldots\|^2$ is a norm of the difference between $z_k$ and $\phi(\hat{x}_k,p)$, and the constraint or the constraints of the set $\Delta$ dictate that the trajectory of the variable $z_k$ should be included in a corridor of uncertainty situated on either side of the trajectory of the estimation $\hat{z}_k$ at least for the majority of the instants k.

Figure 2:
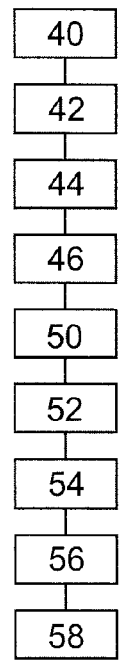
Figure 3:
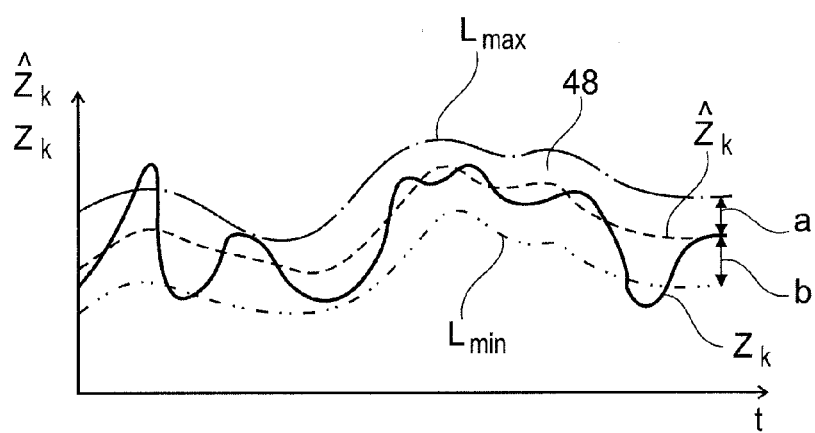

The invention shall be understood more clearly from the following description, given purely by way of a non-exhaustive example and made with reference to the appended drawings of which:

FIG. 1 is a schematic illustration of the architecture of a localizing system including an observer and a system for calibrating this observer, FIG. 2 is a flowchart of a method of calibration of the observer of the system of FIG. 1, and FIG. 3 is a graph illustrating the trajectory of a variable $z_k$ and its estimation $\hat{z}_k$.

Here below in this description, the characteristics and functions well known to those skilled in the art shall not be described in greater detail.

Here, a trajectory designates the variations in time of a variable. The variable that varies in time may be any unspecified variable. In particular, this variable is not necessarily a position in space. For example, it may a temperature or any other physical quantity which varies over time.

FIG. 1 represents a physical system, i.e. in this case an object 4 and a system 8 for localizing this object 4 in the reference system 8.

For example, the object 4 is a probe or a catheter introduced into a human body. The object 4 is mobile in the referential system 8.

The referential system 8 is a fixed referential system having three orthonormal axes X, Y and Z.

The localization of the object 4 in the referential system 8 consists in finding its $x_p$, $y_p$, $z_p$ position and its $\theta_x$, $\theta_y$ and $\theta_z$ orientation. The angles $\theta_x$, $\theta_y$ and $\theta_z$ represent the orientation of the object 4 respectively in relation to the axes X, Y and Z.

To localize the object 4, the system 6 herein comprises magnetic field sources and magnetic field sensors some of which are linked to the referential system 8 while others are fixed without any degree of freedom to the object 4 to be localized. Here, the magnetic field sensor 10 is linked without any degree of freedom to the object 4. The sensor 10 is for example a triaxial sensor, i.e. a sensor capable of measuring the projection of the magnetic field on three non-colinear measurement axes. Such a sensor measures the direction of the magnetic field. More generally, this sensor also measures the amplitude of the magnetic field.

For example, the measurement axes are mutually orthogonal. These axes are fixedly linked to the object 4.

This sensor 10 is connected by means of a flexible wire link to a processing unit 12.

The unit 12 is also connected to three sources 14 to 16 of the magnetic field. These sources are for example magnetic field triaxial sources. A magnetic field triaxial source emits a magnetic field, along three mutually non-colinear emission axes. For example, such a source is formed by several aligned magnetic field uniaxial emitters, respectively on each of the emission axes of the source. The uniaxial emitter mainly emits the magnetic field along a single axis. For example, it is a coil whose turns are wound about a same emission axis. In this case, the emission axis coincides with the winding axis of the turns.

Here, the sources 14 to 16 are identical to each other. These sources are fixed in the referential system 8.

The processing unit 12 powers the sources 14 to 16 with alternating current to generate the magnetic field measured by the sensor 10. The unit 12 also acquires the measurements of the magnetic field made by the sensor 10.

The unit 12 is equipped with an observer 18 which localizes the object 4 in the referential system 8 from the measurements acquired. Here, the observer 18 determines the position and orientation of the object 4 by resolving a system of equations. This system of equations is obtained by modeling the magnetic interactions between the sources 14 to 16 and the sensor 10. In this system of equations, the position $x_p$, $y_p$ and $z_p$ and the orientations $\theta_x$, $\theta_y$ and $\theta_z$ of the object 4 are the unknown quantities while the values of the other parameters are obtained from measurements made by the sensor 10. Further information on such systems of equations may for example be found in the patent application EP 1 502 544.

Here, the observer 18 is a Kalman filter.

This observer 18 builds an estimation $\hat{x}_k$ of a state variable $x_k$ from a measurement $y_k$. The variable $x_k$ is a vector containing the position $x_p$, $y_p$, $z_p$ of the object 4 and its orientation $\theta_x$, $\theta_y$ and $\theta_z$ in the orthonormal referential system 8, the measurement $y_k$ is a measurement vector comprising the measurements made along the three measurement axes of the sensor 10 at an instant k.

The equations of the Kalman filter of the observer 18 are the following:

$$\left\{ \begin{array}{l} \hat{x}_{k+1/k} = F_k \hat{x}_k \\ P_{k+1/k} = F_k P_{k/k} F_k^T + Q_k \end{array} \right\} \quad (1)$$

$$\left\{ \begin{array}{l} \hat{x}_{k+1/k+1} = \hat{x}_{k+1/k} + K_{k+1}(y_{k+1} - C_{k+1}\hat{x}_{k+1/k}) \\ P_{k+1/k+1} = P_{k+1/k} - K_{k+1} C_{k+1} P_{k+1/k} \end{array} \right\} \quad (2)$$

where:

$\hat{x}_{k+1/k}$ is the estimation of the variable $x_k$ obtained solely from data available at the instant k, $F_k$ is the matrix linking the estimation $\hat{x}_k$ to the estimation $\hat{x}_{k+1/k}$, $P_{k/k}$ is the matrix for estimating the covariance, of the errors on the estimation $\hat{x}_k$, $Q_k$ is a matrix of covariance of the noise of the equation of the model containing inter alia the modeling errors, $\hat{x}_{k+1/k+1}$ is the estimation $\hat{x}_{k+1}$ corrected at the instant k+1 from the measurements made at the instant k+1, $y_k$ is the vector of the measurements made at the instant k, $C_k$ is the matrix that links the variable $x_k$ to the measurement $y_k$, $P_{k+1/k+1}$ is the matrix of covariance of the error of estimation $\hat{x}_k$ corrected on the basis of the measurements $y_k$, $K_{k+1}$ is the gain of the Kalman filter.

The matrix $F_k$ is for example obtained by modelizing the magnetic interactions between the sources 14 to 16 and the sensor 10 on the basis of the laws of electromagnetism.

The gain $K_{k+1}$ of the Kalman filter is given by the following relationship:

$$K_{k+1}=P_{k+1/k}C^T_{k+1}[C_{k+1}P_{k+1/k}C^T_{k+1}+R_{k+1}]^{-1} \quad (3)$$

where $R_{k+1}$ is the matrix of covariance of the noise in the measurement $y_k$.

The given equations of the Kalman filter are classic and are therefore not described in greater detail herein.

The use of a Kalman filter gives a precise estimation of the position and orientation of the object 4. However, before this, the matrices $R_k$ and $Q_k$ have to be calibrated, i.e. the values of their coefficients have to be determined. To simplify the description, it is assumed here that the values of these coefficients are constant. The matrices $R_k$ and $Q_k$ are therefore also denoted as R and Q here below.

Here $p_R$ and $p_Q$ denote the set of coefficients respectively of the matrices R and Q to be determined.

Once the Kalman filter has been calibrated, these sets $P_R$ and $P_Q$ are registered in a memory 20 connected to the unit 12 so that they can be used by the observer 18 to estimate the position of the object 4.

FIG. 1 also represents a system 30 for calibrating the observer 18, this system automatically determines the sets $p_R$ and $p_Q$ of coefficients of the matrices R and Q of the observer 18.

To this end, the system 30 is equipped with one or more sensors 32 which measure a variable $z_k$. This variable $z_k$ is a variable whose value is a function of the variable $x_k$. More specifically, the variable $z_k$ is connected to the variable $x_k$ by a known function $\phi$. This function $\phi$ may be a linear function or on the contrary a non-linear function. For example, the sensor 32 measures the acceleration along the X, Y and Z axes of the object 4. In this case, the sensor 32 is formed by several accelerometers.

In another embodiment, the sensor 32 can directly measure the position of the object 4 with sensors other than those used to carry out the measurement $y_k$. For example, the sensor 32 may, to this end, have several cameras or other sensors and other magnetic field sources to measure the position of the object 4. In this particular case, the function $\phi$ is the identity function.

The system 30 also has a computer 34 capable of acquiring the measurements of the sensor 32. This computer 34 is also capable of calibrating the observer automatically by determining the set of coefficients $P_R$ and $P_Q$ from the measurements made by the sensor 32.

In the particular case shown in FIG. 1, the computer 34 is connected to the memory 20 so that it can directly record the set of coefficients $p_R$ and $p_Q$ in this memory 20.

The computer 34 is made with a programmable electronic computer capable of executing the instructions recorded in an information-recording medium. Here, the computer 34 is connected to a memory 36 and this memory 36 contains the instructions needed to execute the method of FIG. 2.

The working of the calibration system 30 shall now be described in greater detail with reference to the method of FIG. 2 and the graph of FIG. 3.

Initially, at a step 40, the relationship $\phi$ which connects the variable $z_k$ to the variable $x_k$ is set up. For example, to this end, the laws of physics are used.

Then, at a step 42, the number of coefficients to be used to calibrate the observer 18 is determined. To this end, knowledge on the physical working of the system 6 is used. Furthermore, this step applies the principle of parsimony according to which the number of coefficients to be calibrated is limited to the greatest possible extent.

For example, in the particular case described herein, it is assumed that the measurements made on each of the measurement axes are independent of one another. Thus, the matrix R is taken to be a diagonal matrix. Similarly, it is assumed that the errors in the state equation are independent. Thus, the matrix Q is taken to be a diagonal matrix. They therefore have the following form:

$$R=\text{diag}(p^1_R,\ldots,p^l_R), p^i_R \geq 0, i=1:l \quad (7)$$

$$Q=\text{diag}(p^1_Q,\ldots,p^n_Q), p^i_Q \geq 0, i=1:n \quad (8)$$

where:
the index i represents the index of the coefficient in the set of coefficients $p_R$ or $p_Q$,
l and n are respectively the dimensions of the matrices R and Q.

Furthermore, the matrices R and Q are symmetrical matrices defined as being positive, i.e. all matrices of which all the Eigen values are positive. To ensure this condition, the matrices R and Q can be written as noted here below:
$R=X^TX$ and $Q=Y^TY$, where the matrices X and Y are diagonal matrices. It can be noted that when the matrices R and Q are any unspecified matrices, the matrices X and Y are higher triangular matrices.

At the end of the step 42, with the assumptions made, the vector p of coefficients to be determined is defined by the following relationship:

$$p=[p^T_R, p^T_Q]^T \quad (9)$$

At a step 44, the criterion to be optimized to determine the vector p is chosen. Here, this vector is given by the following relationship:

$$\min_{p \in \Delta} \left\{ f(p) = \sum_{k=1}^{N} \|z_k - \phi(\hat{x}_k, p)\|^2_2 \right\} \quad (10)$$

where:
$\|\ldots\|_2$ represents the $L_2$ norm operation corresponding to the Euclidian norm,
<<min>> represents the operation of finding the vector p which minimizes the function f(p),
$\Delta$ is the set of constraints that must be verified by the vector p which minimizes the function f(p).

The function $\phi$ which appears in the criterion (10) is the same as the one introduced here above. This function $\phi$ is used to obtain the estimation $\hat{z}_k$ of the variable $z_k$ from the estimation $\hat{x}_k$ as indicated in the following relationship:

$$\hat{z}_k = \phi(\hat{x}_k, p) \quad (11)$$

It will be noted that the function $\phi$ also depends on the vector p since the estimation $\hat{x}_k$ which constitutes the argument of the function $\phi$ is itself a function of the vector p. For this reason, in the above relationship, the estimation $\hat{x}_k$ and the vector p are indicated as the argument of the function $\phi$.

At a step 46, the set $\Delta$ of constraints to be met by the vector p is defined. This set $\Delta$ comprises at least one constraint which dictates that estimation $\hat{z}_k$ and the variable $z_k$ should be proximate to each other. More specifically, this constraint herein dictates that the trajectory of the variable $z_k$ should be included, at least on an average, in a corridor 48 of uncertainty (FIG. 3) situated on either side of the trajectory of estimation $\hat{z}_k$.

This corridor 48 is demarcated by two boundaries $L_{min}$ and $L_{max}$ respectively situated on each side of the trajectory of estimation $\hat{z}_k$. The corridor of uncertainty represents the fact that the estimation $\hat{z}_k$ is only known with an uncertainty attached to it. This uncertainty comes from the fact that there is uncertainty in the estimation $\hat{x}_k$ used to build the estimation $\hat{z}_k$. Thus, to calibrate the observer 18 properly, it is necessary that, for the majority of the instants k, the variable $z_k$ should be included in the corridor 48.

In the particular case shown in FIG. 3, the boundaries $L_{max}$ and $L_{min}$ which demarcate the corridor 48 are separated from the trajectory of $\hat{z}_k$, and respectively by distances a and b. In the case of FIG. 3, these distances a and b are constant in the course of time.

Preferably, the distances a and b are a function of the uncertainty in the estimation $\hat{z}_k$. For example, the distances a and b are all the greater as the mean square deviation $\sigma_{\hat{z}_k}$ is great. $\sigma_{\hat{z}_k}$ is the mean square deviation of the error in the estimation $\hat{z}_k$. For example, here, the set $\Delta$ includes a constraint which dictates that the mean of the divergences between the variable $z_k$ and the estimation $\hat{z}_k$ should be below a predetermined threshold $S_1$. This constraint can be expressed by means of the following relationship:

$$\sqrt{\sum_{k=1}^{N} \|z_k - \hat{z}_k\|_2} \leq S_1 \quad (11)$$

The threshold S1 is for example defined by the following relationship:

$$S_1 = \sqrt{N} \alpha \sigma_{\hat{z}_k} \quad (12)$$

where:
N is the number of instants k, and
$\alpha$ is a constant, for example equal to three.

For each vector p potentially minimizing the criterion (10), it is possible to determine the mean square deviation $\sigma_{\hat{z}_k}$. Indeed, when a vector p is known, the matrices R and Q are also known. From the matrices R and Q, it is possible to compute the matrix $P_{k/k}$ of the covariance of the error in the estimation of $\hat{x}_k$. From this matrix $P_{k/k}$ it is possible to determine the uncertainty affecting the estimation of $\hat{x}_k$. With this uncertainty being known, it is also possible to determine the uncertainty in the estimation $\hat{z}_k$ since the function $\phi$ connecting these two estimations is known. The uncertainty in the estimation $\hat{z}_k$ is then expressed in the form of the mean square deviation $\sigma_{\hat{z}_k}$.

At the step 46, other constraints of the set $\Delta$ may be defined. For example, on the basis of the physical sense of some of the coefficients of the sets $p_R$ and $p_Q$, it is possible to set limits on these coefficients. For example, if pieces of information on the measurement noise of the sensor 10 are known, it is possible on the basis on these pieces of information, to limit the values that can be taken by certain coefficients of the set $p_R$ and $p_Q$.

Once the set $\Delta$ has been defined, in a step 50, the sensor 32 measures the variable $z_k$ at N different instants. The number N of instants is typically greater than the number of coefficients to be determined contained in the vector p.

Once the variables $z_k$ have been measured, they are acquired by the computer 34. Then, a step 52, the different variables and coefficients needed to minimize the criterion (10) are initialized. For example, the initial matrix $P_{0/0}$ of estimation of the covariance in the error of the estimation $\hat{x}_0$ is defined by the following relationship:

$$P_{0/0} = \lambda I, \lambda \gg 1 \quad (13)$$

where:
I is the identity matrix, and
$\lambda$ is a constant.

The constant $\lambda$ is adjusted according to the confidence placed in the initialization of $\hat{x}_0$.

The choice of a constant $\lambda$ far greater than one means that the uncertainty in the initial estimation $\hat{x}_0$ is very great.

Here, the initial estimation $\hat{x}_0$ and the initial value of the coefficients of the vector p are drawn randomly.

Then, a step 54 is performed for determining the vector p which minimizes the criterion (10). In this step, the values of the vector p are made to vary until a vector p is found that minimizes the criterion (10) and at the same time meets the constraints of the set $\alpha$. This step is performed by means of a tool of optimization under constraints. Such tools of optimization under constraints are known. For example such a tool especially is the "Fmincon" function available in the "MATLAB®" development environment, inter alia for digital computation.

Once the vector p which minimizes the criterion (10) has been determined, at the step 56 the values of the coefficients of this vector p are used to calibrate the coefficients of the matrices R and Q of the observer 18. For example, during this step, the values of these coefficients are copied and recorded in the memory 20.

Then, at a step 58, the localizing system 6 uses the coefficients determined by the system 30 to determine the position and orientation of the object 4 from the measurements made by the sensor 10.

Many other embodiments are possible. For example, for a same physical system and for a same observer, it is possible to make different choices on the number of coefficients of this observer that have to be determined in order to calibrate it. For example, the number of coefficients may be even further reduced by requiring that the different coefficients of the diagonal matrix R or Q should all be proportional to a same coefficient. Conversely, the method described here above can also be applied to the case where the matrices Q and R are not diagonal matrices but only positively defined symmetrical matrices. This assumption on the contrary increases the number of coefficients to be determined by the system 30.

In the criterion (10), the Euclidian norm can be replaced by another norm.

Constraints other than those described here above can be used. For example, it is possible to require that the variable $z_k$ should be systematically or routinely included within the corridor of uncertainty 48 at each instant k. This constraint is stronger than the one described with reference to FIG. 3 which requires only that the variable $z_k$ should on an average be included in the corridor of uncertainty 48.

Different sets of constraints can be used at different instants. For example if, at certain instants belonging to a set L, the uncertainty in the measurement of the variable $z_k$ is very low, it is then possible to use a greater constraint at these instants. For example if the instant k belongs to the set L, then it is possible to require that the variable $z_k$ should be routinely included in a more limited corridor of uncertainty. For the instants that do not belong to the set L, the constraint used will be weaker. For example, it will require solely that, on an average, the variable $z_k$ should be included in the corridor of uncertainty 48. The corridor of uncertainty used to define the constraint when the instant k belongs to the set L is not necessarily the same as the one used to define the constraint when the instant k does not belong to this set L.

Additional constraints other than the ones requiring that the variable $z_k$ should be in the corridor of uncertainty of the trajectory of the estimation $\hat{z}_k$ may be used. For example, it is possible to define constraints that dictate a low variation of estimation $\hat{z}_k$ between two successive instants.

Choices other than the ones described above are possible for initializing the optimization of the criterion (10). For example, if the initial value of the variable $x_0$ is known, this value is used to initialize the variable, $x_0$ and the coefficients of the matrix $P_0$ are set as a function of the trust in this value.

The uncertainty on the estimation $\hat{z}_k$ may be obtained by means other than the observations of the observer. For example, this uncertainty may be determined experimentally or on the basis of systems of equations other than those defining the observer 18.

The measured variable $z_k$ and the measurement $y_k$ may coincide. Thus it is not necessary to resort to an additional sensor such as the sensor 32.

The calibration method described here above also applies to the Extended Kalman Filter as well as to the Unscented Kalman Filter (UKF) or any other recursive filter having parameters to be set. More generally, the calibration method described here above can be used to calibrate any observer of a state variable whose coefficients have to be determined beforehand. Thus, the coefficients liable to be determined by means of the above method are not limited to those of a covariance matrix.

The invention has been described in the context of a given application. However, it is not limited to this type of application. Other applications may be taken into account, such as for example applications for obtaining measurements in the probing of seabeds for which the physical system makes it possible to have measurements representing surface/seabed distances or the depths of seas.

The invention claimed is:

1. A method for calibrating coefficients of an observer of a variable state $x_k$ of a physical system from measurements $y_k$ of physical quantities of the system, wherein index k identifies an instant of measurement, the method comprising causing a sensor to measure a variable $z_k$ of the physical system at N different instants, the variable $z_k$ being a function of a state variable $x_k$, and causing a computer to determine a vector p of coefficients that minimizes the following criterion in complying with a predetermined set $\Delta$ of one or more constraints:

$$f(p) = \sum_{k=1}^{N} \|z_k - \phi(\hat{x}_k, p)\|^2$$

wherein $\hat{x}_k$ is an estimation of the variable $x_k$ built by the observer calibrated with the coefficients of the vector p at the instant k, $\phi$ is a known function that links the estimation $\hat{x}_k$ to an estimation $\hat{z}_k$ of the variable $z_k$, $\|\ldots\|^2$ is a norm of the difference between $z_k$ and $\phi(\hat{x}_k, p)$, and the one or more constraints of the predetermined set $\Delta$ dictate that a trajectory of the variable $z_k$ be included in a corridor of uncertainty situated on either side of a path of the estimation $\hat{z}_k$ at least for a majority of the instants k.

2. The method of claim 1, wherein the predetermined set $\Delta$ includes a constraint that dictates that the variable $z_k$ be included between $\hat{z}_k-a$ and $\hat{z}_k+b$, wherein a and b are predetermined positive constants.

3. The method of claim 2, wherein the constants a and b are proportional to a mean square deviation $\sigma_{\hat{z}_k}$ representing uncertainty in the estimation $\hat{z}_k$.

4. The method of claim 1, wherein the predetermined set $\Delta$ of constraints includes a constraint that dictates that a mean of deviations between the variable $z_k$ and its estimation $\hat{z}_k$ be below a predetermined threshold $S_1$.

5. The method of claim 4, wherein the threshold $S_1$ is a function of the uncertainty in the estimation $\hat{z}_k$.

6. The method of claim 1, wherein the observer is a filter selected from a group consisting of a Kalman filter, an extended Kalman filter, and an unscented Kalman Filter, and wherein the coefficients to be calibrated are coefficients of the covariance matrices R and Q of the filter.

7. The method of claim 6, wherein the R and Q matrices are chosen to be diagonal matrices.

8. A manufacture comprising a non-transitory computer-readable medium having encoded thereon software for calibrating coefficients of an observer of a variable state $x_k$ of a physical system from measurements $y_k$ of physical quantities of the system, wherein index k identifies an instant of measurement, the software comprising instructions for causing a sensor to measure a variable $z_k$ of the physical system at N different instants, the variable $z_k$ being a function of a state variable $x_k$, and causing a computer to determine a vector p of coefficients that minimizes the following criterion in complying with a predetermined set $\Delta$ of one or more constraints:

$$\_f(p) = \sum_{k=1}^{N} \|z_k - (\hat{x}_k, p)\|^2$$

wherein $\hat{x}_k$ is an estimation of the variable $x_k$ built by the observer calibrated with the coefficients of the vector p at the instant k, 100 is a known function that links the estimation $\hat{x}_k$ to an estimation $\hat{z}_k$ of the variable $z_k$, $\|\ldots\|^2$ is a norm of the difference between $z_k$ and $\phi(\hat{x}_k, p)$, and the one or more constraints of the predetermined set $\Delta$ dictate that a trajectory of the variable $z_k$ be included in a corridor of uncertainty situated on either side of a path of the estimation $\hat{z}_k$ at least for a majority of the instants k.

9. An apparatus for calibrating coefficients of an observer of a state variable $x_k$ of a physical system from measurements $y_k$ of physical quantities of the system, wherein index k identifies an instant of measurement, the apparatus comprising: at least one sensor capable of measuring a variable $z_k$ of the physical system at N different instants, the variable $z_k$ being a function of a state variable $x_k$, and a computer capable of determining a vector p of coefficients that minimizes the following criterion in complying with a predetermined set $\Delta$ of one or more constraints:

$$f(p) = \sum_{k=1}^{N} \|z_k - (\hat{x}_k, p)\|^2$$

wherein $\hat{x}_k$ an estimation of the variable $x_k$ built by the observer calibrated with the coefficients of the vector p at the instant k, $\phi$ is a known function that links the estimation $\hat{x}_k$ to an estimation $\hat{z}_k$ of the variable $z_k$, $\|\ldots\|^2$ is a norm of the difference between $z_k$ and $\phi(\hat{x}_k, p)$, and the one or more constraints of the predetermined set $\Delta$ dictate that a trajectory of the variable $z_k$ be included in a corridor of uncertainty situated on either side of a path of the estimation $\hat{z}_k$ at least for a majority of the instants k.

* * * * *